(12) United States Patent
Sattlegger et al.

(10) Patent No.: US 7,049,327 B2
(45) Date of Patent: May 23, 2006

(54) SUBSTITUTED DIMETHYL-[1-(1-PHENYL-CYCLOHEXYL)-PIPERIDIN-3-YLMETHYL]-AMINES AND THE USE OF THE SAME AS ANALGESICS

(75) Inventors: Michael Sattlegger, Bonn (DE); Elke Reissmuller, Hiedelfield (DE)

(73) Assignee: Gruenenthal GmbH, Aachen (DE)

( * ) Notice: Subject to any disclaimer, the term of this patent is extended or adjusted under 35 U.S.C. 154(b) by 294 days.

(21) Appl. No.: 10/660,729

(22) Filed: Sep. 12, 2003

(65) Prior Publication Data

US 2004/0127516 A1 Jul. 1, 2004

Related U.S. Application Data

(60) Provisional application No. PCT/EP02/02723, filed on Mar. 13, 2002.

(30) Foreign Application Priority Data

Mar. 14, 2001 (DE) ................ 101 12 198

(51) Int. Cl.
  *A61K 31/445* (2006.01)
  *C07D 211/26* (2006.01)
(52) U.S. Cl. ...................... 514/331; 546/229
(58) Field of Classification Search ........... 514/331; 546/229
  See application file for complete search history.

(56) References Cited

U.S. PATENT DOCUMENTS 4,598,153 A   7/1986 Rice et al. ............. 546/229
5,935,951 A * 8/1999 Ofner et al. ............. 514/227.8
6,673,794 B1* 1/2004 Puetz et al. ............. 514/239.5

FOREIGN PATENT DOCUMENTS

| DE | 2339342 | 8/1973 |
|---|---|---|
| EP | 459387 | 5/1991 |
| WO | WO-98/55478 | 12/1998 |
| WO | WO-00/06545 | 2/2000 |

OTHER PUBLICATIONS

Sattlegger e t al . "Preparation of 2-dimethylamino methyl . . . " CA 137:232563 (2002).*
International Search Report Dated Jul. 26, 2002.
Itzhak et al., "New Analgesic Drugs Derived from Phencyclidine," J. Med. Chem. 1981, 24, 496-499.
Al-Deeb, "Synthesis and Analgesic Activity of New Phencyclidine Derivatives," Arzneim-Forsch./Drug Res. 44 (II) Nr. 10 (1994) pp. 1141-1144.
Raffa et al., "Complementary and Synergistic Antinociceptive Interaction Between the Enantiomers off Tramadol," The Journal of Pharmacology and Experimental Therapeutics, vol. 267, No. 1, pp. 331-340.

* cited by examiner

*Primary Examiner*—Celia Cang
(74) *Attorney, Agent, or Firm*—Crowell & Moring LLP

(57) ABSTRACT

A variety of dimethyl-[1-(1-phenyl-cyclohexyl)-piperidin-3-ylmethyl]-amines are disclosed, along with processes for their preparation, medicaments containing those compounds, and methods for the use of those substances in the preparation of medicaments.

22 Claims, No Drawings

SUBSTITUTED DIMETHYL-[1-(1-PHENYL-CYCLOHEXYL)-PIPERIDIN-3-YLMETHYL]-AMINES AND THE USE OF THE SAME AS ANALGESICS

CROSS-REFERENCE TO RELATED APPLICATIONS

This application is a continuation of International Patent Application No. PCT/EP02/02723, filed on Mar. 13, 2002, designating the United States of America, and published in German as WO 02/072550, the entire disclosure of which is incorporated herein by reference. Priority is claimed based on Federal Republic of Germany Patent Application No. DE 101 12 198.9, filed Mar. 14, 2001.

FIELD OF THE INVENTION

The invention relates to substituted dimethyl-[1-(1-phenyl-cyclohexyl)-piperidin-3-ylmethyl]-amines, to processes for their preparation, to medicaments containing those compounds and to the use of those substances in the preparation of medicaments.

BACKGROUND OF THE INVENTION

Pain is one of the basic clinical symptoms. There is a worldwide need for effective therapies for pain. The urgent need for action for the treatment of chronic and non-chronic pain in a targeted manner which is fair to the patient, which is to be understood as meaning the successful and satisfactory treatment of pain for the patient, is documented in the large number of scientific works which have recently appeared in the field of applied analgesics or the fundamental research into nociception. For example, phencyclidine derivatives having analgesic activity are known from J. Med. Chem. 1981, 24, 496–499 and Arzneim.-Forsch./Drug Res. 44 (II), No. 10 (1994), 1141–1144.

Conventional opioids, such as, for example, morphine, are effective in the therapy of severe to very severe pain. However, they have, inter alia, respiratory depression, vomiting, sedation, constipation and the development of tolerance as undesirable side-effects. In addition, they are less effective in the case of neuropathic or incidental pain, as frequently occurs in tumor patients in particular.

Tramadol hydrochloride—(1RS,2RS)-2-[(dimethylamino)methyl]-1-(3-methoxyphenyl)-cyclohexanol—occupies a special position among the centrally acting analgesics, because that active ingredient brings about pronounced inhibition of pain without the side-effects known for opioids (J. Pharmacol. Exptl. Ther. 267, 33 (1993)).

SUMMARY OF THE INVENTION

The object underlying the invention was to provide substances having analgesic activity which are suitable for the treatment of severe pain, especially for the treatment of chronic and neuropathic pain. In addition, those active ingredients should have as few as possible of the side-effects of the opioid analgesics, such as, for example, nausea, vomiting, dependence, respiratory depression, constipation.

These objects are achieved according to the invention by providing substituted dimethyl-[1-(1-phenyl-cyclohexyl)-piperidin-3-ylmethyl]-amines of the general formula I, which compounds have pronounced analgesic activity.

Accordingly, the invention provides substituted dimethyl-[1-(1-phenyl-cyclohexyl)-piperidin-3-ylmethyl]-amines of the general formula I

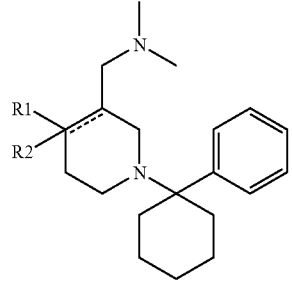

wherein
R1=H, $C_{1-12}$-alkyl (branched, unbranched), vinyl, phenyl (mono- or poly-substituted by $C_{1-5}$-alkyl (branched, unbranched), H, F, Cl, Br, OMe, OEt, OPr, OBu, SMe, OH and/or by $CF_3$),
benzyl (mono- or poly-substituted by $C_{1-5}$-alkyl (branched, unbranched), H, F, Cl, Br, OMe, OEt, OPr, OBu, SMe, OH and/or by $CF_3$),
phenethyl (mono- or poly-substituted by $C_{1-5}$-alkyl (branched, unbranched), H, F, Cl, Br, OMe, OEt, OPr, OBu, SMe, OH and/or by $CF_3$) or
naphthyl (mono- or poly-substituted by $C_{1-5}$-alkyl (branched, unbranched), H, F, Cl, Br, OMe, OEt, OPr, OBu, OBz, SMe, OH and/or by $CF_3$), and
R2=H, F, Cl, Br, OMe, OEt, OPr, OBu, OBz, SMe, OH, $CF_3$ or bond to the double bond, and/or their enantiomers, diastereoisomers, bases or salts of physiologically tolerable acids.

The following substituted dimethyl-[1-(1-phenyl-cyclohexyl)-piperidin-3-ylmethyl]-amines are particularly preferred:

3-dimethylaminomethyl-4-methyl-1-(1-phenyl-cyclohexyl)-piperidin-4-ol or the corresponding dihydrochloride;
3-dimethylaminomethyl-4-ethyl-1-(1-phenyl-cyclohexyl)-piperidin-4-ol or the corresponding dihydrochloride;
3-dimethylaminomethyl-1-(1-phenyl-cyclohexyl)-4-vinyl-piperidin-4-ol or the corresponding dihydrochloride;
4-butyl-3-dimethylaminomethyl-1-(1-phenyl-cyclohexyl)-piperidin-4-ol or the corresponding dihydrochloride;
3-dimethylaminomethyl-4-octyl-1-(1-phenyl-cyclohexyl)-piperidin-4-ol or the corresponding dihydrochloride;
3-dimethylaminomethyl-4-(3-methoxy-phenyl)-1-(1-phenyl-cyclohexyl)-piperidin-4-ol or the corresponding dihydrochloride;
3-dimethylaminomethyl-4-(2-fluoro-phenyl)-1-(1-phenyl-cyclohexyl)-piperidin-4-ol or the corresponding dihydrochloride;
4-(3-chloro-phenyl)-3-dimethylaminomethyl-1-(1-phenyl-cyclohexyl)-piperidin-4-ol or the corresponding dihydrochloride;
4-benzyl-3-dimethylaminomethyl-1-(1-phenyl-cyclohexyl)-piperidin-4-ol or the corresponding dihydrochloride;
3-dimethylaminomethyl-4-phenethyl-1-(1-phenyl-cyclohexyl)-piperidin-4-ol or the corresponding dihydrochloride; and
3-dimethylaminomethyl-4-(3-hydroxy-phenyl)-1-(1-phenyl-cyclohexyl)-piperidin-4-ol or the corresponding dihydrochloride.

The invention further provides a process for the preparation of dimethyl-[1-(1-phenyl-cyclohexyl)-piperidin-3-ylmethyl]-amines of the general formula I, which may have different substituents at R1 and R2. If only either R1 or R2 is present, there is a double bond in the piperidine ring between positions 3 and 4.

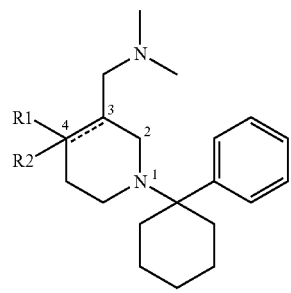

I

The preparation of the compounds according to the invention is carried out in the following steps:

The enamine IV is formed from cyclohexanone II and 1,4-dioxa-8-aza-spiro[4.5]decane III.

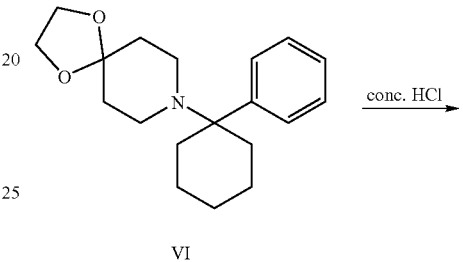

II   III   IV

The enamine IV is directly reacted further with phenyl-magnesium chloride V to form the amine VI:

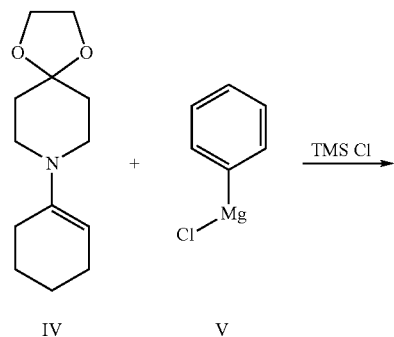

IV   V

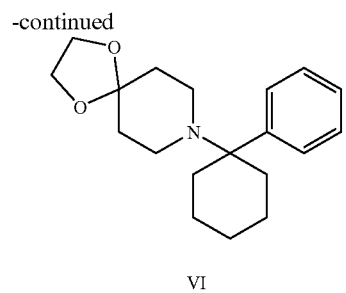

VI

The amine VI is hydrolysed in a further step, and VII is precipitated in the form of the hydrochloride.

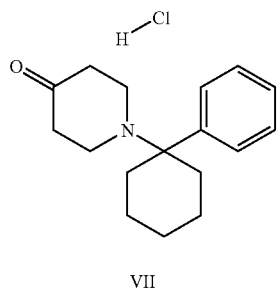

VI

→ conc. HCl

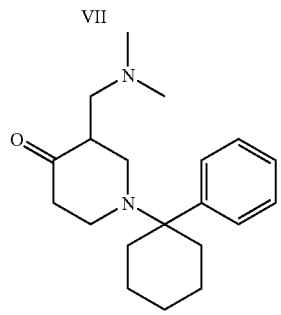

VII

The hydrochloride VII is reacted further with a variant of the Eschenmoser salt VIII to form the Mannich base IX.

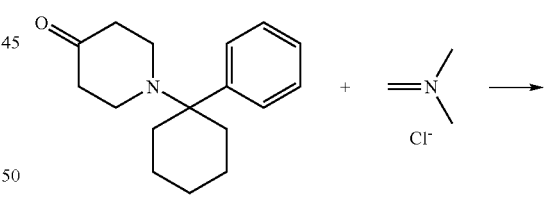

VII   VIII

IX

Reaction with a Grignard reagent X is then carried out to form the products XI.

Compounds of formula XIII may be obtained by dehydrating compounds of formula XI.

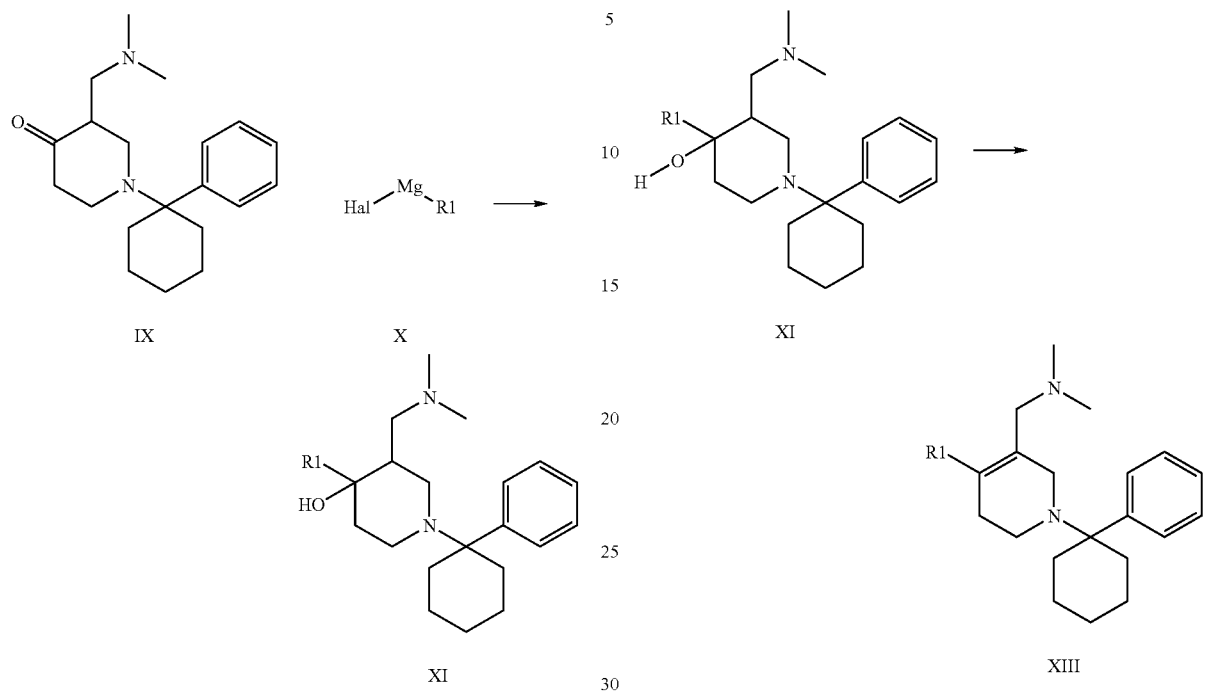

The compounds of the general formula XI can be reacted further with a number of reagents that introduce the above-defined radical R2, especially halogenated hydrocarbons, ethers, esters, ureas, amides, carbonates and related compounds, to form the compounds XII, excepting where R2=OH.

Compounds of formula XIV may be obtained by reducing compounds of formula XIII with hydrogen.

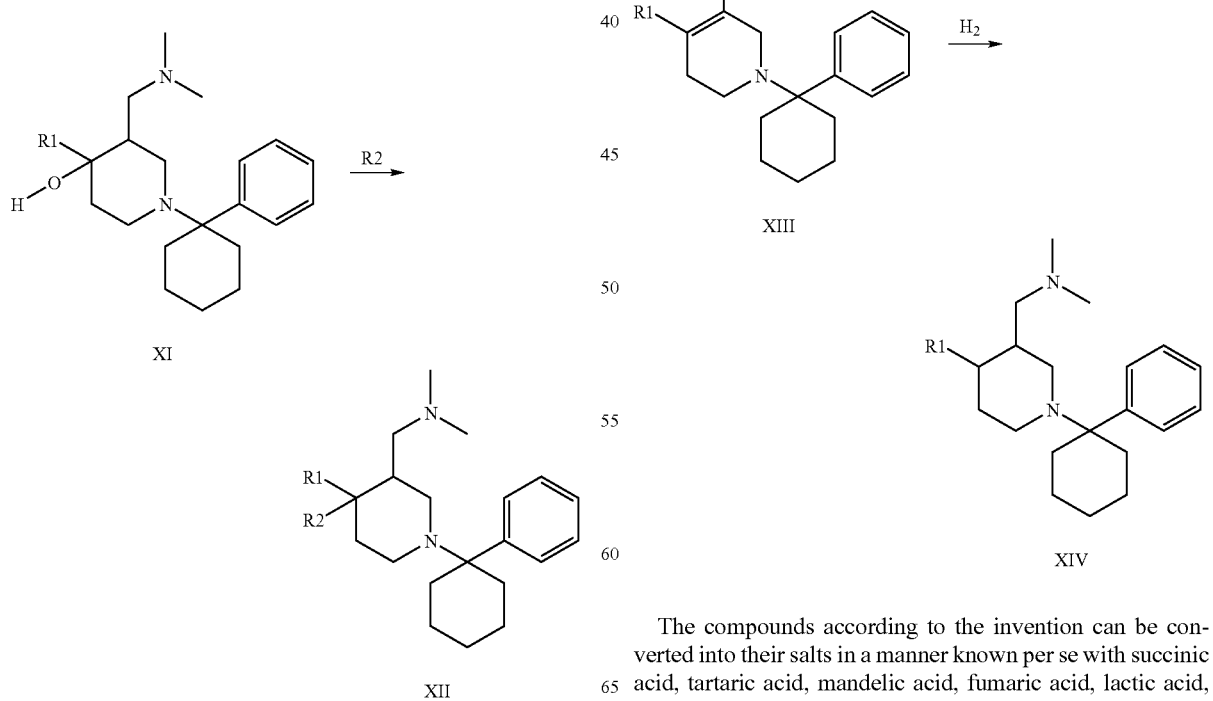

The compounds according to the invention can be converted into their salts in a manner known per se with succinic acid, tartaric acid, mandelic acid, fumaric acid, lactic acid, citric acid, glutamic acid and/or aspartic acid. The salt formation is preferably carried out in a solvent, for example diethyl ether, diisopropyl ether, an alkyl acetate, acetone and/or 2-butanone. Trimethylchlorosilane in methyl ethyl ketone is also suitable for preparing the hydrochlorides.

The substituted dimethyl-[1-(1-phenyl-cyclohexyl)-piperidin-3-ylmethyl]-amines of the general formula I according to the invention are toxicologically harmless and are therefore suitable pharmaceutical active ingredients.

Accordingly, the invention further provides medicaments which contain as active ingredient at least one substituted dimethyl-[1-(1-phenyl-cyclohexyl)-piperidin-3-ylmethyl]-amine of the general formula I and/or their enantiomers, diastereoisomers, bases or salts of physiologically tolerable acids.

The medicaments preferably contain enantiomeric mixtures of the active ingredient in non-equimolar amounts, one of the enantiomers having a relative content in the mixture of from 5 to 45 weight %.

The medicaments according to the invention are suitable for controlling pain.

Accordingly, the invention relates also to the use of at least one substituted dimethyl-[1-(1-phenyl-cyclohexyl)-piperidin-3-ylmethyl]-amine of the general formula I and/or its enantiomers, diastereoisomers, bases or salts of physiologically tolerable acids, in the preparation of a medicament for controlling pain.

For the preparation of corresponding pharmaceutical formulations there are used, in addition to at least one substituted dimethyl-[1-(1-phenyl-cyclohexyl)-piperidin-3-ylmethyl]-amine of the general formula I, carriers, fillers, solvents, diluents, colorants and/or binders. The choice of auxiliary substances, and the amounts thereof to be used, depend on whether the medicament is to be administered orally, intravenously, intraperitoneally, intradermally, intramuscularly, intranasally, buccally or locally, for example to infections of the skin, of the mucosa and of the eyes. There are suitable for oral administration preparations in the form of tablets, dragées, capsules, granules, drops, juices and syrups, and for parenteral and topical administration and for administration by inhalation there are suitable solutions, suspensions, readily reconstitutable dry preparations, and also sprays. Suitable preparations for percutaneous administration are compounds of the general formula I according to the invention in a depot formulation in dissolved form or in a plaster, optionally with the addition of agents promoting penetration of the skin. Forms of preparation for oral or percutaneous administration may release the compounds of the general formula I according to the invention in a delayed manner.

The amount of active ingredient to be administered to the patient varies in dependence on the weight of the patient, the mode of administration, the indication and the severity of the disease. From 50 to 500 mg/kg of at least one dimethyl-[1-(1-phenyl-cyclohexyl)-piperidin-3-ylmethyl]-amine of the general formula I are usually administered.

EXAMPLES

General Remarks

The Examples which follow serve to illustrate the invention in greater detail, but do not limit the general idea underlying the invention.

The yields of the prepared compounds have not been optimised.

All melting points are uncorrected.

Unless indicated otherwise, petroleum ether having a boiling range of from 50 to 70° C. has been used. Ether means diethyl ether.

Silica gel 60 (0.040 to 0.063 mm) from E. Merck, Darmstadt was used as the stationary phase for the column chromatography.

The thin-layer chromatographic investigations were carried out using commercial HPLC plates, silica gel 60 F 254, from E. Merck, Darmstadt.

The mixing ratios of the eluants for all the chromatographic investigations are always given in volume/volume.

Example 1

3-Dimethylaminomethyl-4-methyl-1-(1-phenyl-cyclohexyl)-piperidin-4-ol dihydrochloride (1)

1$^{st}$ Step

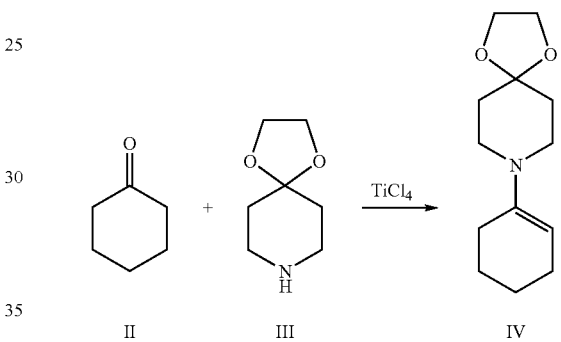

II   III   IV

For the preparation of 8-cyclohex-1-enyl-1,4-dioxa-8-aza-spiro[4.5]decane IV, 54 ml (0.5 mol.) of cyclohexanone were dissolved with 200 ml (1.5 mol.) of 1,4-dioxa-8-aza-spiro[4.5]decane III in 0.5 liter of diethyl ether, and the solution was stirred for half an hour. 31 ml of titanium tetrachloride in 0.5 liter of n-hexane were then added dropwise at 0° C. in the course of 60 minutes. When the addition was complete, the mixture was slowly heated to 20° C. and then stirred for 24 hours. The resulting precipitate was filtered off with suction and discarded. The filtrate was concentrated and reacted further directly. The yield was 83 g (0.37 mol., 71%).

2$^{nd}$ Step

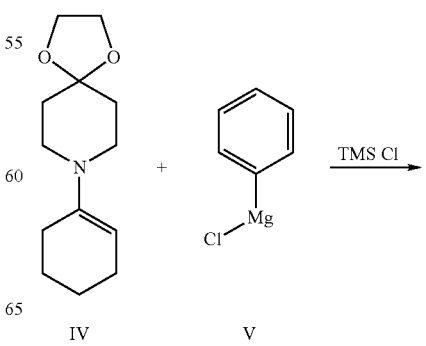

IV   V

-continued

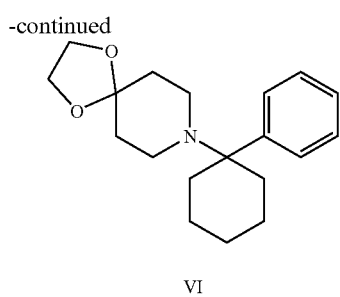

VI 83 g (0.37 mol.) of 8-cyclohex-1-enyl-1,4-dioxa-8-azaspiro[4.5]decane IV were reacted with 200 ml of 2M phenylmagnesium chloride solution V. To that end, 52 ml of trimethylchlorosilane in 0.75 liter of methylene chloride were placed in a reaction vessel with 2 ml of water, and the enamine IV was added dropwise. The Grignard reagent was then added, while cooling with an ice bath, and the whole was stirred for 3 hours. Hydrolysis was then carried out with 200 ml of ammonium chloride solution, and the aqueous phase was extracted with 0.5 liter of methylene chloride. The product VI was purified by column chromatography on silica gel using diisopropyl ether. The yield was 36 g (0.12 mol., 32%).

$3^{rd}$ Step

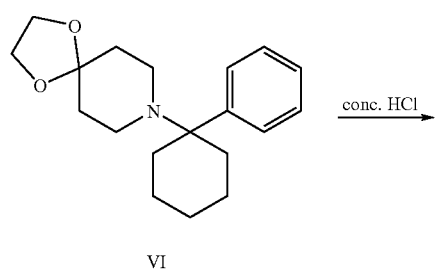

VI conc. HCl

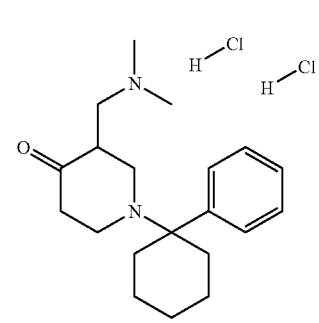

VII

The amine VI was hydrolysed in a further step and precipitated in the form of the hydrochloride VII. To that end, 250 ml of concentrated HCl were added at 20° C. to 36 g (0.12 mol.) of VI, followed by stirring for 12 hours. The mixture was rendered alkaline with ammoniacal solution and extracted with diethyl ether. The free base was precipitated in the form of the hydrochloride using trimethylchlorosilane. The yield was 21 g (0.072 mol., 60%).

$4^{th}$ Step

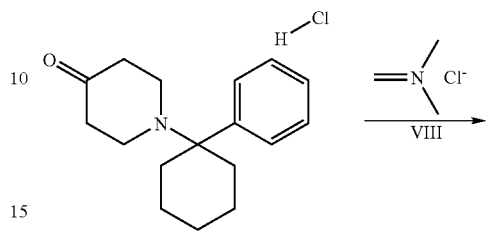

VII         VIII

IX

The hydrochloride VII was reacted with a variant of the Eschenmoser salt VIII to form the Mannich base IX. In that reaction, 6.0 g (20 mmol.) of compound VII were stirred for 48 hours at 20° C. with 2.1 g (22 mmol.) of compound VIII in 50 ml of dry tetrahydrofuran. The reaction mixture was then poured into a basic, aqueous ammoniacal solution, and the free base of IX was extracted with 3×100 ml of methylene chloride. The organic phases were combined and dried, and the solvent was removed in vacuo. The residue was dissolved in 50 ml of methyl ethyl ketone, and 5 ml of trimethylsilyl chloride were added thereto. 3.0 g (8 mmol., 40%) of compound IX were obtained.

$5^{th}$ Step

After the freeing of the hydrochloride IX into the free base, IX was reacted with a methylmagnesium chloride X to form XI and, after precipitation in the form of the dihydrochloride, to form (1).

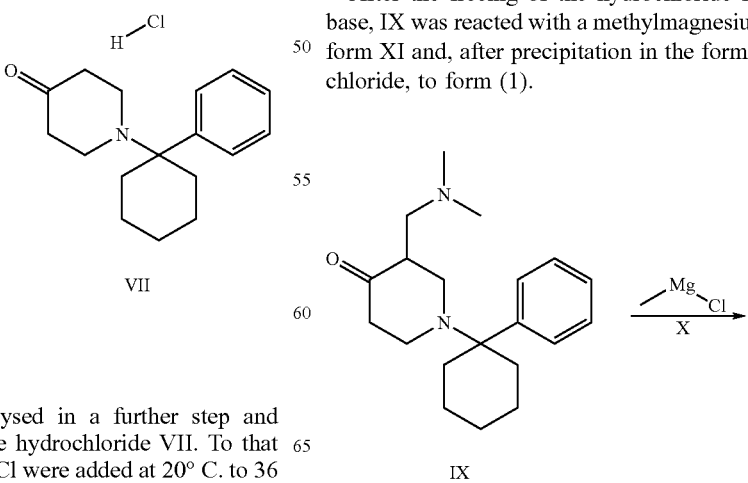

IX

-continued

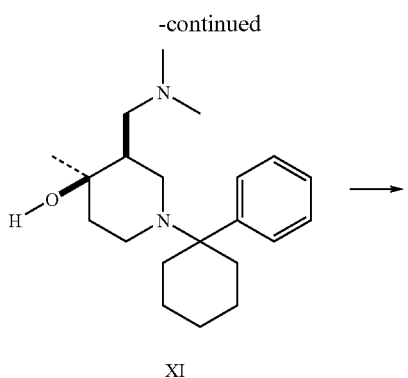

XI

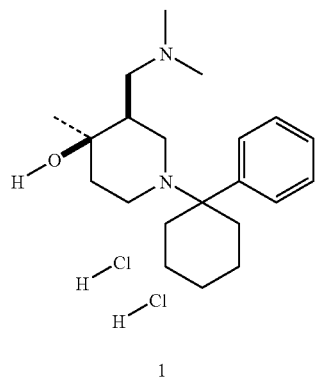

1

To that end, 0.57 g (1.8 mmol.) of IX was dissolved in 2.5 ml of tetrahydrofuran and cooled to −20° C. Under protecting gas, 1.0 ml (3 mmol.) of 3M methylmagnesium chloride solution in tetrahydrofuran (THF) was added, and stirring was carried out overnight. 2 ml of ammonium chloride solution were then added for the purposes of hydrolysis, and the aqueous phase was extracted with ether. After precipitation in the form of the dihydrochloride, the yield of (1) was 0.2 g (0.3 mmol., 16%). The decomposition point of compound (1) was 220° C.

Example 2

3-Dimethylaminomethyl-4-ethyl-1-(1-phenyl-cyclohexyl)-piperidin-4-ol dihydrochloride (2)

The synthesis instructions are described under Example 1. Ethylmagnesium chloride was used instead of methylmagnesium chloride. In the reaction of 0.57 g (1.8 mmol.) of IX, the yield of (2) was 21 mg (0.036 mmol., 2%). The compound decomposed at 190° C. and above.

Example 3

3-Dimethylaminomethyl-4-vinyl-1-(1-phenyl-cyclohexyl)-piperidin-4-ol dihydrochloride (3)

The synthesis instructions are described under Example 1. Vinylmagnesium chloride was used instead of methylmagnesium chloride. In the reaction of 0.57 g (1.8 mmol.) of IX, the yield of (3) was 37 mg (0.09 mmol., 3%). The compound decomposed at 190° C. and above.

Example 4

4-Butyl-3-dimethylaminomethyl-1-(1-phenyl-cyclohexyl)-piperidin-4-ol dihydrochloride (4)

The synthesis instructions are described under Example 1. Butylmagnesium chloride was used instead of methylmagnesium chloride. In the reaction of 0.57 g (1.8 mmol.) of IX, the yield of (4) was 37 mg (0.09 mmol., 3%). The melting point of the compound was 225° C.

Example 5

4-Octyl-3-dimethylaminomethyl-1-(1-phenyl-cyclohexyl)-piperidin-4-ol dihydrochloride (5)

The synthesis instructions are described under Example 1. Octylmagnesium chloride was used instead of methylmagnesium chloride. In the reaction of 0.57 g (1.8 mmol.) of IX, the yield of (5) was 104 mg (0.22 mmol., 12%).

Example 6

3-Dimethylaminomethyl-4-(3-methoxyphenyl)-1-(1-phenyl-cyclohexyl)-piperidin-4-ol dihydrochloride (6)

The synthesis instructions are described under Example 1. 3-Methoxy-phenylmagnesium bromide was used instead of methylmagnesium chloride. In the reaction of 0.57 g (1.8 mmol.) of IX, the yield of (6) was 491 mg (1.07 mmol., 60%). The melting point of the compound was 245° C.

Example 7

3-Dimethylaminomethyl-4-(2-fluoro-phenyl)-1-(1-phenyl-cyclohexyl)-piperidin-4-ol dihydrochloride (7)

The synthesis instructions are described under Example 1. 2-Fluoro-phenylmagnesium iodide was used instead of methylmagnesium chloride. In the reaction of 0.57 g (1.8 mmol.) of IX, the yield of (7) was 267 mg (0.55 mmol., 31%). The compound decomposed at 96° C. and above.

Example 8

3-Dimethylaminomethyl-4-(3-chloro-phenyl)-1-(1-phenyl-cyclohexyl)-piperidin-4-ol dihydrochloride (8)

The synthesis instructions are described under Example 1. 3-Chloro-phenylmagnesium iodide was used instead of methylmagnesium chloride. In the reaction of 0.57 g (1.8 mmol.) of IX, the yield of (8) was 177 mg (0.35 mmol., 19%). The compound decomposed at 96° C. and above.

Example 9

3-Dimethylaminomethyl-4-(benzyl)-1-(1-phenyl-cyclohexyl)-piperidin-4-ol dihydrochloride (9)

The synthesis instructions are described under Example 1. Benzylmagnesium chloride was used instead of methylmagnesium chloride. In the reaction of 0.57 g (1.8 mmol.) of IX, the yield of (9) was 213 mg (0.48 mmol., 27%).

Example 10

3-Dimethylaminomethyl-4-(phenethyl)-1-(1-phenyl-cyclohexyl)-piperidin-4-ol dihydrochloride (10)

The synthesis instructions are described under Example 1. Phenylmagnesium bromide was used instead of methylmagnesium chloride. In the reaction of 0.57 g (1.8 mmol.) of IX, the yield of (10) was 255 mg (0.56 mmol., 31%). The compound decomposed at 234° C. and above.

Example 11

3-Dimethylaminomethyl-4-(3-hydroxy-phenyl)-1-(1-phenyl-cyclohexyl)-piperidin-4-ol dihydrochloride (11)

The synthesis instructions are described analogously to Example 6, except for the last step. The methyl ether was then cleaved into the phenol. To that end, 0.5 g (1.2 mmol.) of the free base of compound (6) was dissolved in 5 ml of toluene, and 10 ml of dibutylaluminium hydride solution (1.5 M in toluene) were added at 0° C. and under a nitrogen atmosphere. After 12 hours' stirring, the batch was hydrolysed with 5 ml of ethyl acetate and 5 ml of ethanol, the solvent was removed in vacuo, the residue was dissolved in methyl ethyl ketone, and 1.0 ml of trimethylsilyl chloride was added thereto. The yield of (11) was 71 mg (0.15 mmol., 12%). The compound melted between 245 and 248° C.

Pharmacological Studies

Writing Test in Mice

The analgesic activity of the compounds according to the invention in the phenylquinone-induced writhing test, modified according to I. C. Hendershot, J. Forsaith in J. Pharmacol. Exp. Ther. 125, 237–240 (1959), was studied in mice. Male mice weighing from 25 to 30 g were used for that purpose. Groups of 10 animals per substance dose were each given, 10 minutes after the intravenous administration of the test substances, 0.3 ml/mouse of a 0.02% aqueous solution of phenylquinone (phenylbenzoquinone, Sigma, Deisenhofen; preparation of the solution with addition of 5% ethanol and storage in a water bath at 45° C.), administered intraperitoneally. The animals were then placed individually in observation cages. By means of a push-button counter, the number of pain-induced stretching movements (so-called writhing reactions=straightening of the body with stretching of the rear extremities) was counted 5 to 20 minutes following the administration of the phenylquinone. Animals that had been given only physiological saline with phenylquinone were used as control.

All the substances were tested in the standard dose of 10 mg/kg. The percentage inhibition (% inhibition) of the writhing reactions by a substance was calculated according to the following formula:

$$\% \text{ inhibition} = 100 - \left[\frac{\text{writhing reaction treated animals}}{\text{writhing reaction control}} \times 100\right]$$

All the compounds according to the invention which were studied exhibited moderately pronounced to pronounced analgesic activity.

The results of selected writhing studies are summarized in Table 1.

TABLE 1

Analgesia test in the writhing test in mice

| Example No. | % inhibition of the writhing reactions 10 mg/kg i.v. |
|---|---|
| 1 | 33 |
| 5 | 31 |
| 6 | 54 |
| 8 | 40 |
| 9 | 35 |
| 11 | 73 |

Formalin Test, Mice

Studies to determine the antinociceptive activity of compounds 6 and 11 according to the invention were carried out in the formalin test on male mice (NMRI, 20 to 30 g).

In the formalin test, a distinction is made between the first (early) phase (0 to 15 minutes after the formalin injection) and the second (late) phase (15 to 60 minutes after the formalin injection) (D. Dubuisson, S. G. Dennis, Pain 4, 161–174 (1977)). The early phase, as a direct reaction to the formalin injection, represents a model for acute pain, while the late phase is regarded as a model for persistent (chronic) pain (T. J. Coderre, J. Katz, A. L. Vaccarino, R. Melzack, Pain 52, 259–285 (1993)).

The compounds according to the invention were studied in the second phase of the formalin test, in order to obtain information regarding the activity of substances in the case of chronic/inflammatory pain.

By means of a single subcutaneous formalin injection (20 μl, 1%) into the dorsal side of the right rear paw, a nociceptive reaction was induced in free-moving test animals; the nociceptive reaction manifests itself in pronounced licking and biting of the affected paw.

For the test period of three minutes in the second (late) phase of the formalin test (21st to 24th minute following formalin administration), the nociceptive behaviour was recorded continuously by observation of the animals. The pain behaviour was quantified by adding the number of seconds for which the animals exhibited licking and biting of the affected paw during the test period. After injection of substances that have antinociceptive activity in the formalin test, the described behaviours of the animals are reduced and in some cases even eliminated. A comparison was made with control animals that had received vehicle (solvent) prior to the formalin administration. On the basis of the quantification of the pain behaviour, the action of the substance in the formalin test was determined as a change relative to the control in percent. The time of administration prior to the formalin injection was chosen in dependence on the mode of administration of the compounds according to the invention (intravenous: 5 minutes).

The results of selected studies in the formalin test in mice are summarized in Table 2 below.

TABLE 2

Antinociceptive activity of the compounds according to the invention in the formalin test in mice

| Example No. | % inhibition relative to control 10 mg/kg i.v. |
|---|---|
| 6 | 55 |
| 11 | 59 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted dimethyl-[1-(1-phenyl-cyclohexyl)-piperidin-3-ylmethyl]-amine compound corresponding to formula I

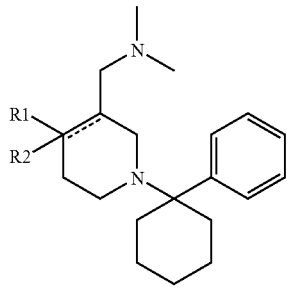

wherein
R1=H, $C_{1-12}$-alkyl (branched or unbranched), vinyl, phenyl (mono- or poly-substituted by at least one substitutent independently selected from the group consisting of $C_{1-5}$-alkyl (branched or unbranched), H, F, Cl, Br, O-methyl, O-ethyl, O-propyl, O-butyl, S-methyl, OH, and $CF_3$),
  benzyl (mono- or poly-substituted by at least one substitutent independently selected from the group consisting of $C_{1-5}$-alkyl (branched or unbranched), H, F, Cl, Br, O-methyl, O-ethyl, O-propyl, O-butyl, S-methyl, OH, and $CF_3$),
  phenethyl (mono- or poly-substituted by at least one substitutent independently selected from the group consisting of $C_{1-5}$-alkyl (branched or unbranched), H, F, Cl, Br, O-methyl, O-ethyl, O-propyl, O-butyl, S-methyl, OH, and $CF_3$), or
  naphthyl (mono- or poly-substituted by at least one substitutent independently selected from the group consisting of $C_{1-5}$-alkyl (branched or unbranched), H, F, Cl, Br, O-methyl, O-ethyl, O-propyl, O-butyl, O-benzyl, S-methyl, OH, and $CF_3$), and R2=H, F, Cl, Br, O-methyl, O-ethyl, O-propyl, O-butyl, O-benzyl, S-methyl, OH, $CF_3$, or R2 represents a bond as part of a double bond in the adjacent ring;

or a salt thereof with a physiologically tolerated acid.

2. A compound according to claim 1, wherein R1 and R2 are bound to a chiral carbon atom, and said compound is present in the form of an isolated enantiomer or an isolated diastereoisomer.

3. A compound according to claim 1, wherein R1 and R2 are bound to a chiral carbon atom, and said compound is present in the form of a mixture of enantiomers or diastereoisomers.

4. A compound according to claim 1, wherein said compound is present in the form of a free base.

5. A compound according to claim 1, wherein R1 is unbranched $C_{1-8}$-alkyl.

6. A compound according to claim 1, wherein R1 is vinyl.

7. A compound according to claim 1, wherein R1 is a phenyl radical substituted by F, Cl, OH or O-methyl.

8. A compound according to claim 1, wherein R1 is benzyl.

9. A compound according to claim 1, wherein R1 is phenethyl.

10. A compound according to claim 1, wherein R2 is OH.

11. A compound according to claim 1, wherein said compound is:
  3-dimethylaminomethyl-4-methyl-1-(1-phenyl-cyclohexyl)-piperidin-4-ol or the corresponding dihydrochloride;
  3-dimethylaminomethyl-4-ethyl-1-(1-phenyl-cyclohexyl)-piperidin-4-ol or the corresponding dihydrochloride;
  3-dimethylaminomethyl-1-(1-phenyl-cyclohexyl)-4-vinyl-piperidin-4-ol or the corresponding dihydrochloride;
  4-butyl-3-dimethylaminomethyl-1-(1-phenyl-cyclohexyl)-piperidin-4-ol or the corresponding dihydrochloride;
  3-dimethylaminomethyl-4-octyl-1-(1-phenyl-cyclohexyl)-piperidin-4-ol or the corresponding dihydrochloride;
  3-dimethylaminomethyl-4-(3-methoxy-phenyl)-1-(1-phenyl-cyclohexyl)-piperidin-4-ol or the corresponding dihydrochloride;
  3-dimethylaminomethyl-4-(2-fluoro-phenyl)-1-(1-phenyl-cyclohexyl)-piperidin-4-ol or the corresponding dihydrochloride;
  4-(3-chloro-phenyl)-3-dimethylaminomethyl-1-(1-phenyl-cyclohexyl)-piperidin-4-ol or the corresponding dihydrochloride;
  4-benzyl-3-dimethylaminomethyl-1-(1-phenyl-cyclohexyl)-piperidin-4-ol or the corresponding dihydrochloride;
  3-dimethylaminomethyl-4-phenethyl-1-(1-phenyl-cyclohexyl)-piperidin-4-ol or the corresponding dihydrochloride; or
  3-dimethylaminomethyl-4-(3-hydroxy-phenyl)-1-(1-phenyl-cyclohexyl)-piperidin-4-ol or the corresponding dihydrochloride.

12. A process for the preparation of a compound of formula XII, XIII, or XIV,

XII

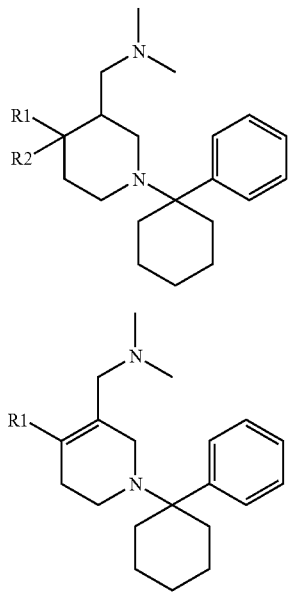

XIII

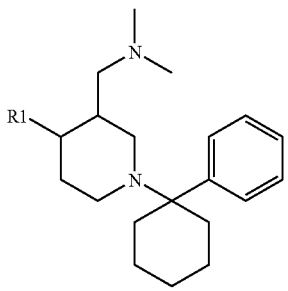

XIV wherein
R1=H, $C_{1-12}$-alkyl (branched or unbranched), vinyl, phenyl (mono- or poly-substituted by at least one substituent independently selected from the group consisting of $C_{1-5}$-alkyl (branched or unbranched), H, F, Cl, Br, O-methyl, O-ethyl, O-propyl, O-butyl, S-methyl, OH, and $CF_3$),
   benzyl (mono- or poly-substituted by at least one substituent independently selected from the group consisting of $C_{1-5}$-alkyl (branched or unbranched), H, F, Cl, Br, O-methyl, O-ethyl, O-propyl, O-butyl, S-methyl, OH, and $CF_3$),
   phenethyl (mono- or poly-substituted by at least one substituent independently selected from the group consisting of $C_{1-5}$-alkyl (branched or unbranched), H, F, Cl, Br, O-methyl, O-ethyl, O-propyl, O-butyl, S-methyl, OH, and $CF_3$), or
   naphthyl (mono- or poly-substituted by at least one substituent independently selected from the group consisting of $C_{1-5}$-alkyl (branched or unbranched), H, F, Cl, Br, O-methyl, O-ethyl, O-propyl, O-butyl, O-benzyl, S-methyl, OH, and $CF_3$), and
R2=H, F, Cl, Br, O-methyl, O-ethyl, O-propyl, O-butyl, O-benzyl, S-methyl, $CF_3$, or R2 represents a bond as part of a double bond in the adjacent ring, said process comprising the steps of:
   reacting a cyclohexanone (formula II) with 1,4-dioxa-8-aza-spiro[4.5]decane (formula III) in the presence of titanium tetrachloride to form an enamine of formula IV;

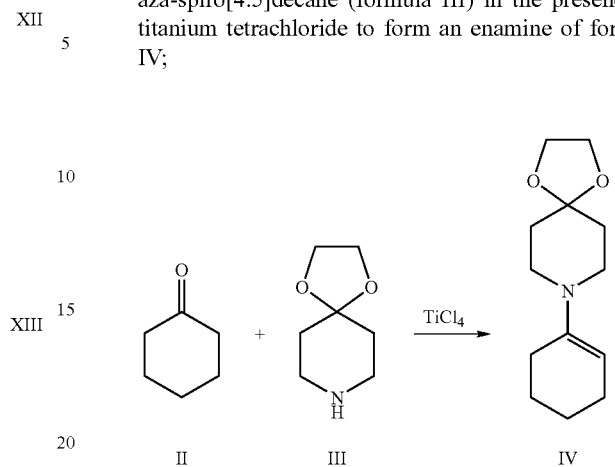

II    III    IV reacting the enamine of formula IV with phenylmagnesium chloride (formula V) in the presence of trimethylchlorosilane to form an amine of formula VI;

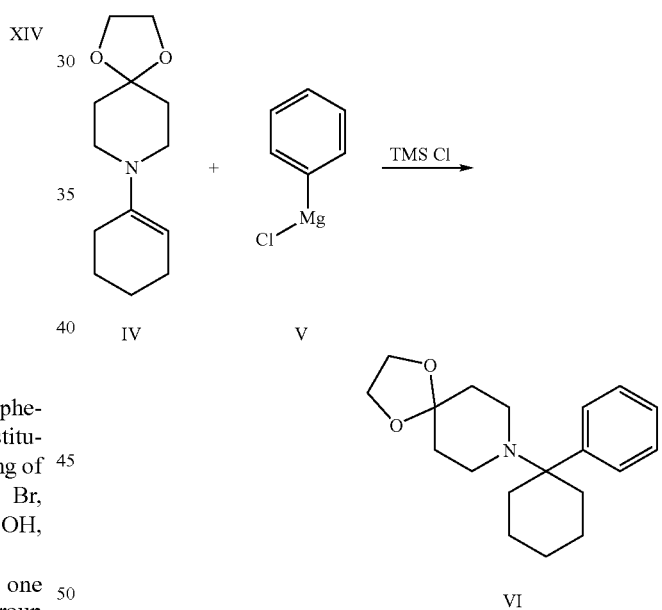

IV    V

VI hydrolyzing and precipitating the amine of formula VI to form a hydrochloride of formula VII;

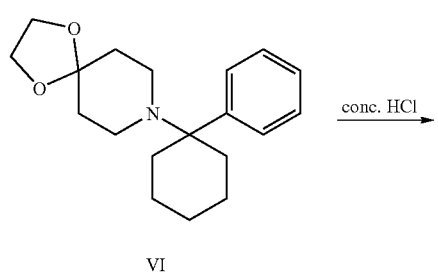

VI

-continued

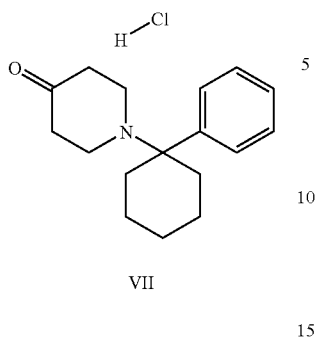

VII reacting the hydrochloride of formula VII with a variant of an Eschenmoser salt according to formula VIII to form a Mannich base of formula IX;

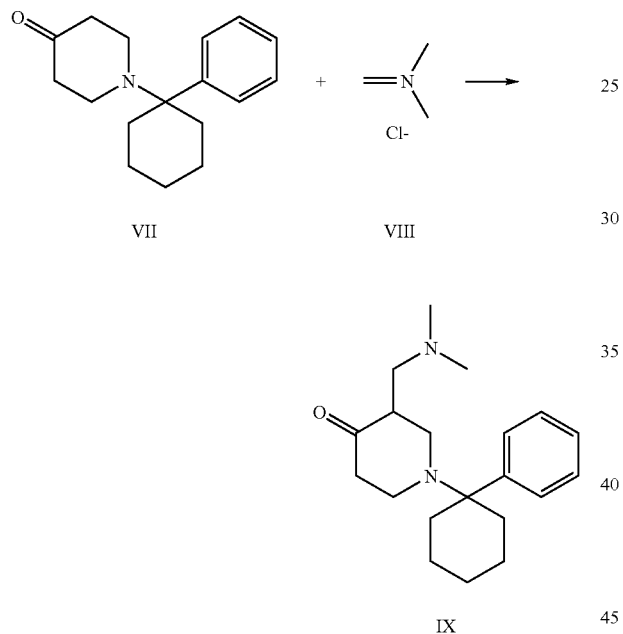

VII         VIII

IX reacting the Mannich base of formula IX with a Grignard reagent of formula X, which has the organic radical R1, to form a compound of formula XI;

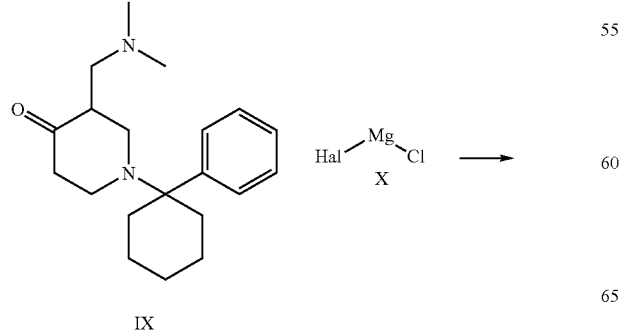

IX

-continued

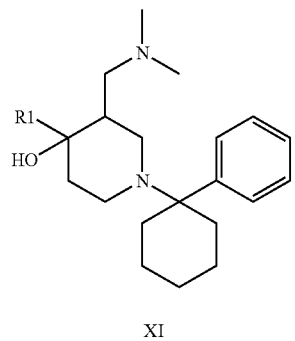

XI purifying the compounds of formula XI and isolating the compounds of formula XI in the form of salts of physiologically tolerable acids, wherein:

compounds of formula XII are obtained by reacting compounds of formula XI with reagents that replace the OH group in the 4-position of the compounds of formula XI by the radical R2;

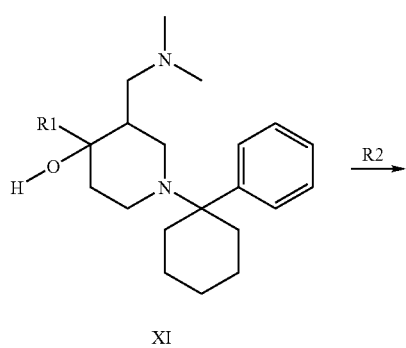

XI

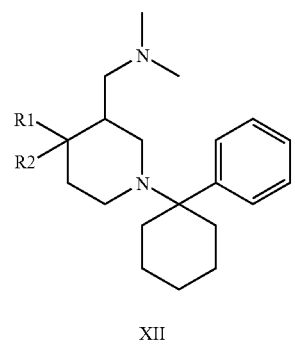

XII compounds of formula XIII are obtained by dehydrating compounds of formula XI;

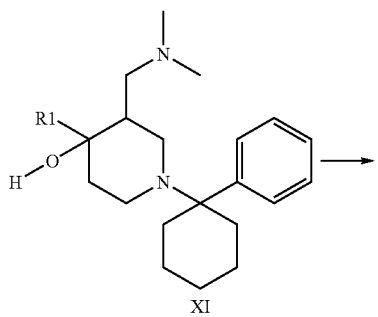

XI

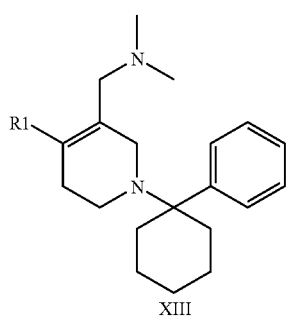

XIII or compounds of formula XIV are obtained by reducing compounds of formula XIII with hydrogen;

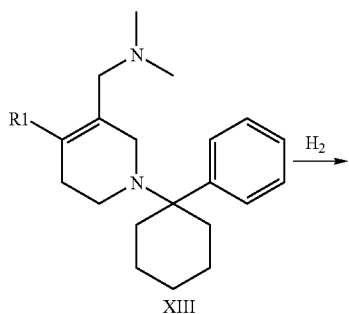

XIII

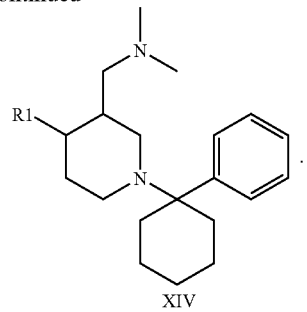

XIV

13. A pharmaceutical composition comprising as an active ingredient a pharmaceutically effective amount of a compound according to claim 1 and a pharmaceutically acceptable carrier or adjuvant.

14. A pharmaceutical composition according to claim 13 wherein said active ingredient is present as a mixture of the enantiomers of a compound corresponding to formula I containing a chiral carbon atom, wherein the two enantiomers are not present in equimolar amounts.

15. A pharmaceutical composition according to claim 14, wherein one of the enantiomers has a content of from 5 to 45% in the enantiomeric mixture.

16. The pharmaceutical composition of claim 13 wherein said compound is present in the form of an isolated enantiomer or an isolated diastereoisomer.

17. The pharmaceutical composition of claim 13 wherein said compound is present in the form of a mixture of enantiomers or diastereoisomers.

18. The pharmaceutical composition of claim 13 wherein said compound is present in the form of a free base.

19. A method of alleviating pain in a mammal, said method comprising administering to said mammal an effective pain alleviating amount of a compound according to claim 1.

20. The method of claim 19 wherein said compound is administered in the form of an isolated enantiomer or an isolated diastereoisomer.

21. The method of claim 19 wherein said compound is administered in the form of a mixture of enantiomers or diastereoisomers.

22. The method of claim 19 wherein said compound is administered in the form of a free base.

* * * * *